United States Patent
Tsuzuki et al.

(10) Patent No.: US 7,094,602 B2
(45) Date of Patent: Aug. 22, 2006

(54) METHOD FOR CELL CULTURE

(75) Inventors: Hirohiko Tsuzuki, Minami-ashigara (JP); Kazuhiro Aikawa, Minami-ashigara (JP); Akiko Matsuura, Minami-ashigara (JP)

(73) Assignee: Fuji Photo Film Co, Ltd., Kanagawa (JP)

( * ) Notice: Subject to any disclaimer, the term of this patent is extended or adjusted under 35 U.S.C. 154(b) by 145 days.

(21) Appl. No.: 10/690,568

(22) Filed: Oct. 23, 2003

(65) Prior Publication Data

US 2004/0137619 A1    Jul. 15, 2004

(30) Foreign Application Priority Data

Oct. 24, 2002  (JP) .............................. 2002-309123

(51) Int. Cl.
*C12N 5/00* (2006.01)

(52) U.S. Cl. .................................................... 435/378

(58) Field of Classification Search ................ None
See application file for complete search history.

(56) References Cited

U.S. PATENT DOCUMENTS 5,292,525 A * 3/1994 Brenden et al. ............ 424/601
6,821,107 B1 * 11/2004 Hara et al. .................. 425/397

OTHER PUBLICATIONS

Esser S et al. "Copper complexation index as a polarographic summation parameter for the determination of chelating agents in water". Fresenius J. Anal. Chem., 2000, 368(2-3): 250-5. Entire document.*

* cited by examiner

*Primary Examiner*—Sandra E. Saucier
*Assistant Examiner*—Satyendra K. Singh
(74) *Attorney, Agent, or Firm*—Sughrue Mion, PLLC (57) ABSTRACT

A method for detaching a carrier for cell culture from cultured cells formed on a surface of said carrier, which includes the step of bringing the carrier for cell culture into contact with a compound represented by the following formula (I) or a polyphosphoric acid or a salt thereof: $MO_3P-L^{11}-PO_3M$ wherein $L^{11}$ represents a divalent bridging group; and M represents a hydrogen atom or a cation. The carrier preferably includes a calcium alginate layer and a cell adhesion gel layer.

10 Claims, 1 Drawing Sheet

FIG. 1

METHOD FOR CELL CULTURE

FIELD OF THE INVENTION

The present invention relates to a method for cell culture.

RELATED ART

When cell culture is performed by using a carrier for cell culture, a method has so far been know generally, as a method of transferring cells for subculture from one carrier to other carrier, in which cells are collected from a carrier by a treatment with a mixed solution of an enzyme, such as trypsin as a typical example, and a chelating reagent, and the cells are added to a new carrier for transfer (for example, see, Watanabe T., Saibo Kogaku (Cell Engineering), Separate volume, "Me de Miru Jikken Note Series" (Visual Experimental Note Series), "Bio Jikken Illustrated" (Bioengineering Experiment Illustrated), Vol, (6), "Sukusuku Sodate Saibo Baiyo" (Quick Grow of Cell Culture), Shujun-sha, 1996; "Shin Seikagaku Jikken Koza" (Lecture of New Biochemical Experiments), Vol. 18, "Saibo Baiyo Gijutsu" (Cell Culture Techniques), edited by the Japanese Biochemical Society, 1990). Further, it has been attempted to have cells exhibit organ-like functions by co-culture of two or more kinds of cells (for example, see, Yamato M., Okano M., "Rinsho Geka" (Journal of Clinical Surgery), 56 (1), 58–60, 2001). This cell lamination method comprises the steps of culturing cells by using a carrier for cell culture, which comprises a porous membrane on which an alginic acid gel layer and an extracellular matrix component gel layer or extracellular matrix component sponge layer are laminated, and then dissolving the alginic acid gel layer by using an aqueous solution of a chelating agent to detach a cell culture from the carrier for cell culture, and further carrying out a culture by using the cell cultures in combination (for example, see, Japanese Patent Unexamined Publication (KOKAI) No. 2001-120267).

As the chelating reagent used for the detachment of these cell cultures, EDTA is generally used, and few examples using GEDTA are also known. However, EDTA and GEDTA have strong stimulation on cells, and thus they cause problems of suppression of cell growth, deformation of cells and the like. Stimulation on cells may highly possibly induce canceration or abnormal differentiation of cells particularly in a culture of stem cells and an organ construction, which have recently been focused as organ regeneration techniques or cell therapies, and thus causes serious problems.

DISCLOSURE OF THE INVENTION

An object of the present invention is to provide means for easily detaching cultured cells from a carrier for cell culture without inhibiting growth or proliferation of the cells or inducing abnormal differentiation of the cells. Another object of the present invention is to provide a method for laminating cell layers by using such means to prepare cell culture. In order to achieve the aforementioned objects, the inventors of the present invention conducted various researches. As a result, they found that, when a compound represented by the following formula (I) was used, cultured cells can be most easily detached from a carrier for cell culture, and absolutely no abnormality was observed in the detached cells.

Thus, the present invention provides a method for detaching a carrier for cell culture from cultured cells formed on a surface of the carrier for cell culture, which comprises the step of bringing the carrier for cell culture into contact with a compound represented by the following formula (I):

wherein $L^{11}$ represents a divalent bridging group; and M represents hydrogen atom or a cation, or a polyphosphoric acid or a salt thereof. Preferably, provided are the aforementioned method, wherein the carrier for cell culture comprises a calcium alginate gel layer, and the aforementioned method, wherein the carrier for cell culture comprises laminated calcium alginate gel layer and cell adhesion gel layer.

The present invention also provides a method for culturing cells by using a carrier for cell culture, which comprises the following steps of:

(1) bringing a cell culture containing cultured cells adhered on a surface of the carrier for cell culture into contact with a compound represented by the aforementioned formula (I), or a polyphosphoric acid or a salt thereof, and (2) detaching the cultured cells from the cell culture and transplanting the cells on a surface of other cultured cells.

According to preferred embodiments of these inventions, there are provided the aforementioned methods, wherein $L^{11}$ is a substituted or unsubstituted divalent hydrocarbon group; the aforementioned methods, wherein the divalent hydrocarbon group is a substituted or unsubstituted methylene group; the aforementioned methods, wherein the compound represented by the formula (I) is a compound represented by the following formula (II):

wherein $V^{21}$, $L^{22}$, and $L^{23}$ independently represent a divalent hydrocarbon group; $R^{21}$ and $R^{22}$ independently represent a substituted or unsubstituted alkyl group, or a substituted or unsubstituted aryl group; and M represents hydrogen atom or a cation; and the aforementioned methods, wherein the compound represented by the formula (I) is a compound represented by the following formula (III):

wherein $L^{31}$, $L^{32}$, $L^{33}$, $L^{34}$, and $L^{35}$ represent a divalent hydrocarbon group; and M represents hydrogen atom or a cation.

From another aspect, the present invention provides a method for transferring cells, which comprises the following steps of:

(1) culturing cultured cells formed on a carrier for cell culture while the cultured cells are allowed to be in contact with a surface of other carrier for cell culture with weighting; and (2) bringing a cell culture obtained in the aforementioned step (1) into contact with a compound represented by the aforementioned formula (I), or a polyphosphoric acid or a salt thereof to detach the carrier for cell cultures. According to preferred embodiments, the carrier for cell culture is that comprising a calcium alginate gel layer, and the carrier for cell culture comprising a calcium alginate gel layer comprises laminated calcium alginate gel layer and cell adhesion gel layer.

From further aspect, the present invention provides a method for laminating cell layers, which comprises the following steps of.
(1) culturing cultured cello formed on a carrier for cell culture while the cultured cells are allowed to be in contact with other cultured cells with weighting; and
(2) bringing a cell culture obtained in the aforementioned step (1) into contact with a compound represented by the aforementioned formula (I), or a polyphosphoric acid or a salt thereof to detach the carrier for cell culture. According to preferred embodiments, the carrier for cell culture comprises a calcium alginate gel layer, and the carrier for cell culture comprising a calcium alginate gel layer comprises laminated calcium alginate gel layer and cell adhesion gel layer. According to these inventions, the weighting is preferably performed via a sponge.

From further aspects, the present invention provides cell cultures, transferred cells, and laminated cell layers that can be obtained by the aforementioned methods. Further, the present invention also provides a detachment agent for detaching cultured cells from a cell culture obtained by cell culture using a carrier for cell culture, preferably a carrier for cell culture comprising a calcium alginate gel layer, which contains a compound represented by the aforementioned formula (I), or a polyphosphoric acid or a salt thereof, a remover for removing a carrier for cell culture, preferably a carrier for cell culture comprising a calcium alginate gel layer, from a cell culture obtained by cell culture using said carrier for cell culture, which contains a compound represented by the aforementioned formula (I), or a polyphosphoric acid or a salt thereof, and a dissolving agent for calcium alginate gel, which contains a compound represented by the aforementioned formula (I), or a polyphosphoric acid or a salt thereof.

According to the method of the present invention, cultured cells can be most conveniently and surely detached from a carrier for cell culture without damaging the cultured cells, and transfer and lamination of cells can be surely performed.

PREFERRED EMBODIMENTS OF THE INVENTION

The cation represented by M is an organic or inorganic cation, and examples include, for example, alkali metal ions (lithium ion, sodium ion, potassium ion, cesium ion and the like), alkaline earth metal ions (magnesium ion, calcium ion and the like), ammonium ions (ammonium, trimethylammonium, triethylammonium, tetramethylammonium, tetraethylammonium, tetrabutylammonium, 1,2-ethinediammonium ions and the like), pyridinium ion, imidazolium ion, phosphonium ions (tetrabutylphosphonium ion and the like). M is preferably hydrogen atom, an alkali metal ion, or an ammonium ion, more preferably sodium ion or potassium ion.

The type of $L^{11}$ is not particularly limited so long as the group is a divalent bridging group. For example, a divalent hydrocarbon group can be preferably used, Examples of the divalent hydrocarbon group include, for example, linear, branched and cyclic alkylene groups, and alkylene groups consisting of a combination thereof. An alkylene group having preferably 1 to 10 carbon atoms, more preferably 1 to 6 carbon atoms, still more preferably 1 to 8 carbon atoms, can be used. More specically, examples include methylene, ethylene, trimethylene, propylene, ethylethylene, hexamethylene, 1,2-cyclohexylene and the like. Examples of the divalent hydrocarbon group other than alkylene groups include an alkenylene group having preferably 2 to 10 carbon atoms, more preferably 2 to 6 carbon atoms, still more preferably 2 to 4 carbon atoms (e.g., vinylene, propenylene and the like), an alkynylene group having preferably 2 to 30 carbon atoms, more preferably 2 to 20 carbon atoms, still more preferably 2 to 16 carbon atoms (e.g., ethynylene, 3-pentynylene and the like), an arylene group having preferably 6 to 20 carbon atoms, more preferably 6 to 16 carbon atoms, still more preferably 6 to 12 carbon atoms (e.g., phenylene, naphthylene and the like), an aralkylene group having preferably 7 to 20 carbon atoms, more preferably 7 to 16 carbon atoms, still more preferably 7 to 12 carbon atoms (e.g., xylylene and the like) and the like. As the divalent hydrocarbon group represented by $L^{11}$, an alkylene group or an arylene group can be preferably used. More preferred is an alkylene group, still more preferred are methylene, ethylene, propylene, and butylene, and particularly preferred is methylene.

When the bridging group represented by $L^{11}$ is a divalent hydrocarbon group, the hydrocarbon group may have one or more substituents which may be same or different. Examples of the substituents include an alkyl group having preferably 1 to 20 carbon atoms, more preferably 1 to 12 carbon atoms, particularly preferably 1 to 8 carbon atoms (e.g., methyl, thyl, isopropyl, tert-butyl, n-octyl, n-decyl, n-hexadecyl, cyclopropyl, cyclopentyl, cyclohexyl and the like, the same shall apply hereafter in the present specification), an alkenyl group having preferably 2 to 20 carbon atoms, more preferably 2 to 12 carbon atoms, particularly preferably 2 to 8 carbon atoms (e.g., vinyl, allyl, 2-butenyl, 3-pentenyl and the like), an alkynyl group having preferably 2 to 20 carbon atoms, more preferably 2 to 12 carbon atoms, particularly preferably 2 to 8 carbon atoms (e.g., 1-propynyl, 3-pentynyl and the like), an aryl group having preferably 6 to 30 carbon atoms, more preferably 6 to 20 carbon atoms, particularly preferably 6 to 12 carbon atoms (e.g., phenyl, p-methylphenyl, naphthyl and the like, the same will be given hereafter in the specification), an amino group having preferably 0 to 20 carbon atoms, more preferably 0 to 10 carbon atoms, particularly preferably 0 to 6 carbon atoms (e.g., amino, methylamino, dimethylamino, diethylamino, dibenzylamino and the like), an alkoxyl group having preferably 1 to 20 carbon atoms, more preferably 1 to 12 carbon atoms, particularly preferably 1 to 8 carbon atoms (e.g., methoxy, ethoxy, butoxy and the like), an aryloxy group having preferably 6 to 20 carbon atoms, more preferably 6 to 16 carbon atoms, particularly preferably 6 to 12 carbon atoms (e.g., phenyloxy, 2-naphthyloxy and the like), an acyl group having preferably 1 to 20 carbon atoms, more preferably 1 to 16 carbon atoms, particularly preferably 1 to 12 carbon atoms (e.g., acetyl, benzoyl, formyl, pivaloyl and the like), an alkoxycarbonyl group having preferably 2 to 20 carbon atoms, more preferably 2 to 16 carbon atoms, particularly preferably 2 to 12 carbon atoms (e.g., methozycarbonyl, ethoxycarbonyl and the like), an aryloxycarbonyl group having preferably 7 to 20 carbon atoms, more preferably 7 to 16 carbon atoms, particularly preferably 7 to 10 carbon atoms (e.g., phenyloxycarbonyl and the like), an acyloxy group having preferably 2 to 20 carbon atoms, more preferably 2 to 16 carbon atoms, particularly preferably 2 to 10 carbon atoms (e.g., acetoxy, benzoyloxy and the like), an acylamino group having preferably 2 to 20 carbon atoms, more preferably 2 to 16 carbon atoms, particularly preferably 2 to 10 carbon atoms (e.g., acetylamino, benzoylamino and the like), an alkoxycarbonylamino group having preferably 2 to 20 carbon atoms, more preferably 2 to 16 carbon atoms, particularly preferably 2 to 12 carbon atoms (e.g., methoxycarbonylamino and the like), an aryloxycarbonylamino group having preferably 7 to 20 carbon atoms, more preferably 7 to 16 carbon atoms, particularly preferably 7 to 12 carbon atoms (e.g., phenyloxycarbonylamino and the like), a sulfonylamino group having preferably 1 to 20 carbon atoms, more preferably 1 to 16 carbon atoms, particularly preferably 1 to 12 carbon atoms (e.g., methanesulfonylamino, benzenesulfonylamino and the like), a sulfamoyl group having preferably 0 to 20 carbon atoms, more preferably 0 to 16 carbon atoms, particularly preferably 0 to 12 carbon atoms (e.g., sulfamoyl, methylaulfamoyl, dimethylsulfamoyl, phenylsulfamoyl and the like), a carbamoyl group having preferably 1 to 20 carbon atoms, more preferably 1 to 16 carbon atoms, particularly preferably 1 to 12 carbon atoms (e.g., carbamoyl, methylcarbamoyl, diethylcarbamoyl, phenylcarbamoyl and the like), an alkylthio group having preferably 1 to 20 carbon atoms, more preferably 1 to 16 carbon atoms, particularly preferably 1 to 12 carbon atoms (e.g., methylthio, ethylthio and the like), an arylthio group having preferably 6 to 20 carbon atoms, more preferably 6 to 16 carbon atoms, particularly preferably 6 to 12 carbon atoms (e.g., phenylthio and the like), a sulfonyl group having preferably 1 to 20 carbon atoms, more preferably 1 to 16 carbon atoms, particularly preferably 1 to 12 carbon atoms (e.g., mesyl, tosyl and the like), a sulfonyl group having preferably 1 to 20 carbon atoms, more preferably 1 to 16 carbon atoms, particularly preferably 1 to 12 carbon atoms (e.g., methanesulfinyl, benzenesulfinyl and the like), a ureido group having preferably 1 to 20 carbon atoms, more preferably 1 to 16 carbon atoms, particularly preferably 1 to 12 carbon atoms (e.g., ureido, methylureido, phenylureido and the like), a phosphoramido group having preferably 1 to 20 carbon atoms, more preferably 1 to 16 carbon atoms, particularly preferably 1 to 12 carbon atoms (e.g., diethylphosphoramido, phenylphosphoramido and the like), hydroxy group, mercapto group, a halogen atom (e.g., fluorine atom, chlorine atom, bromine atom, iodine atom), cyano group, sulfo group, carboxyl group; nitro group, hydroxamic acid group, sulfino group, hydrazino group, a heterocyclic group (e.g., imidazolyl, pyridyl, furyl, piperidyl, morpholino and the like) and the like. These substituents may be substituted with other one or more substituents.

When the bridging group represented by $L^{11}$ is a divalent hydrocarbon group, and the hydrocarbon group has one or more substituents which may be the same or different, preferred examples of the substituents include an alkyl group, an aryl group, an alkoxyl group, an aryloxy group, an alkylthio group, an arylthio group, an acyl group, an alkoxycarbonyl group, an aryloxycarbonyl group, an acyloxy group, an acylamino group, an alkoxycarbonylamino group, an aryloxyearbonylamino group, a sulfonylamino group, a sulfamoyl group, a carbamoyl group, a ureido group, hydroxy group, a halogen atom, cyano group, and a heterocyclic group, More preferred are an alkyl group and hydroxy group, and particularly preferred are those disubstituted with an alkyl group and hydroxy group. An example is where the compound represented by the formula (I) is 1-hydroxyethane-1,1-diphosphoric acid, and this compound can be most suitably used for the present invention.

In the methods of the present invention, a polyphosphoric acid or a salt thereof can be preferably used. The polyphosphoric acid is preferably a linear condensed polyphosphoric acid obtained by dehydration condensation of orthophosphoric acid, a polyphosphoric acid having a side chain introduced with an organic group into the side chain, a cyclic polyphosphoric acid and the like, In particular, linear condensed polyphosphoric acids represented by the formula $(P_nO_{8n+1})H_{n+2}$ (n represents an integer) are preferred in which two or more of $PO_4$ tetrahedrons share vertex oxygen atoms to form a linear structure. A salt of polyphosphoric acid means a polyphosphoric acid having a molecular structure in which hydrogen of hydroxyl group of the polyphosphoric acid is replaced with a cation. The cation is an organic or inorganic cation, and examples include, for example, alkali metal ions (lithium ion, sodium ion, potassium ion, cesium ion and the like), alkaline earth metal ions (magnesium ion, calcium ion and the like), ammonium ions (ammonium, trimethylammonium, triethylammonium, tetramethylammonium, tetraethylammonium, tetrabutylammonium, 1,2-ethanediammonium ions and the like), pyridinium ion, imidazolium ion, phosphonium ions (tetrabutylphosphonium ion and the like) and the like. The cation is preferably hydrogen ion, alkali metal ion, or ammonium ion, more preferably sodium or potassium ion. Symbol "n" is an integer of at least 2, preferably 2 to 2000, still more preferably 5 to 2000.

Other preferred examples include the compounds represented by the formula (II) or the formula (III). As divalent hydrocarbon groups represented by $L^{21}$, $L^{22}$, $L^{23}$, $L^{31}$, $L^{32}$, $L^{33}$, $L^{34}$, and $L^{35}$ in the compounds represented by the formula (II) or (III), those explained for the aforementioned formula (I) can be used. However, they preferably represent an alkylene group or an arylene group, more preferably an alkylene group, still more preferably methylene, ethylene, propylene, butylene, or cyclohexylene, particularly preferably ethylene or propylene. The divalent hydrocarbon groups represented by $L^{21}$, $L^{22}$, and $L^{23}$ may have one or more substituents, and as such substituents, the substituents mentioned for the compounds wherein $L^{11}$ in the aforementioned formula (I) is a divalent hydrocarbon group can be used. The divalent hydrocarbon groups represent d by $L^{21}$, $L^{22}$, $L^{23}$, $L^{31}$, $L^{32}$, $L^{33}$, $L^{34}$, and $L^{35}$ are preferably unsubstituted hydrocarbon groups, $L^{21}$, $L^{22}$, and $L^{23}$ may be the same or different. It is preferred that $L^{21}$ and $L^{22}$ are the same groups. $L^{31}$, $L^{32}$, $L^{33}$, $L^{34}$, and $L^{35}$ may be the same or different. It is preferred that $L^{31}$, $L^{32}$, $L^{33}$, and $L^{34}$ are the same groups.

The cation represented by M in the formula (II) or (III) is an organic or inorganic cation, and examples include, for example, hydrogen ion, alkali metal ions (lithium ion, sodium ion, potassium ion, cesium ion and the like), alkaline earth metal ions (magnesium ion, calcium ion and the like), ammonium ions (ammonium, trimethylammonium, triethylammonium, tetramethylammonium, tetraethylammonium, tetrabutylammonium, 1,2-ethanediammonium ions and the like), pyridinium ion, imidazolium ion, phosphonium ions (tetrabutylphosphonium ion and the like). M is preferably hydrogen ion, or an alkali metal ion, more preferably an alkali metal ion.

$R^{21}$ and $R^{22}$ represent a substituted or unsubstituted alkyl group, or a substituted or unsubstituted aryl group, and they preferably represent a substituted alkyl group. Examples of the substituent of the alkyl group include, for example, an aryl group, an alkoxyl group, an aryloxy group, an alkylthio group, an arylthio group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, a ureido group, hydroxy group, a halogen atom, cyano group, a heterocyclic group, carboxyl group, sulfonic acid group, and phosphonic acid group, and carboxyl group, sulfonic acid group, and phosphonic acid group are more preferred.

The types of cells that can be treated by the methods of the present invention are not particularly limited, and the methods can be used for, for example, various cultured animal cells. More specifically, the methods can be applied for primary culture cells or cells of established cell lines derived from various organs such as liver, kidney, lung, stomach, and spleen, primary culture cells or cells of established cell lines derived from tissues such as nerve, muscle, skin, and bones as well as various cancer cells. As animal cells, cells of any animals including arthropods (insects) can be used, and cells of for example, germs and embryos can also be used. Examples include, for example, embryonic stem cells, somatic stem cell, neural stem cells, epithelial keratinocytes, melanocytes, vascular endothelial cells, vascular smooth muscle cells, hair metrocytes, osteoblasts, chondrocytes, hepatocytes, stellate cells, small hepatocytes, amnion-derived cells, fetal liver-derived cells, fetal kidney-derived cells, and fetal lung-derived cells, as well as, as cells of established cell lines, HeLa cells, FL cells, KB cells, HepG2 cells, WI-88 cells, MA104 cells, BSC-1 cells, Vero cells, CV-1 cells, BHK-21 cells, L cells, CHL cells, BAE cells, BRL cells, PAE cell and the like. The genes of these cells may be artificially manipulated.

For the cell culture, a culture medium (for example, D-MEM medium, MEM medium, HamF12 medium, or HamF10 medium) containing cells at a density of from 10,000 to 15,000 cells/ml is usually added onto the surface of the carrier for cell culture. The cell culture conditions can be appropriately chosen by those skilled in the art depending on the type of cells to be cultured. In general, the culture may preferably be continued until a confluent cell monolayer is formed on the surface of the carrier for cell culture.

The kind of carrier for cell culture used in the method of the present invention is not particularly limited. A carrier comprising calcium alginate gel is preferred. More preferred is, for example, a carrier for cell culture having a laminated structure wherein a cell adhesion gel layer is provided on a calcium alginate gel layer. Further, the calcium alginate gel layer is preferably formed on a surface of porous membrane. Hereafter, a carrier for cell culture comprising a calcium alginate gel layer will be specifically explained. However, the carrier for call culture used for the methods of the present invention is not limited to this specific embodiment.

The gelation of calcium alginate may be performed in a conventional manner, for example, by using ion exchange. For example, when calcium ions are added to an aqueous solution of sodium alginate, ion exchange quickly occurs to give calcium alginate gel. More specifically, a calcium alginate gel layer can be obtained by adding from 0.3 to 0.5 ml of a 0.2 to 2% sodium alginate aqueous solution to a cell having a bottom composed of porous membrane (e.g., membrane having a pore size of 3.0 microns produced by FALCON), then allowing a 0.01 to 0.1 M calcium chloride aqueous solution to infiltrate from the porous membrane, and leaving the system at 20 to 30° C. for 0.5 to 1 hour. By performing the gelation of alginic acid using the porous membrane as described above, a carrier for cell culture can be obtained which comprises the porous membrane and an alginic acid gel layer laminated on the porous membrane. However, the use of the porous membrane for the gelation of alginic acid is not essential for the method of the present invention.

In the specification, a "porous membrane" means a membrane which does not allow passage of calcium alginate gel but allows passage of the compounds of the formula (I). The type of the porous membrane is not particularly limited so long as it has the aforementioned property, and a membrane having small pores, as well as a membrane having voids and that having both of small pores and voids and the like are included. Specific examples of the porous membrane include, for example, filter paper, ultrafiltration membranes, silicone rubber membranes, tetrafluoroethylene resin porous membranes CPTFE porous membranes), non-woven fabric, gauze-like mesh, various membrane filters (nylon, polyvinylidene fluoride, acetylcellulose, cellulose nitrate, polyethylene terephthalate, polycarbonate and the like), and preferred are membrane filters, in particular, membranes of nylon membrane filters. When the porous membrane has small pores, the sizes of pores are not particularly limited so long as the sizes do not allow passage of alginic acid gel but allow passage of the compounds of the formula (I). The sizes are usually from 0.02 to 1,000 μm, preferably from 0.02 to 100 μm, more preferably from 0.1 to 10 μm.

The dry thickness of the calcium alginate gel layer is preferably from 0.1 to 10 μm, more preferably from 0.5 to 5 μm. When a solid content of the alginic acid gel layer is too small, a satisfactory gel membrane can not be formed, which may result in formation of holes. When a solid content of the alginic acid gel layer is too large, problems may arise in that curling or cracks may be formed in a dried membrane, or deformation during culture step and poor dissolution in alginic acid gel dissolution step may be caused. The thickness of the alginic acid gel layer is preferably measured under a sufficiently dried condition, and the thickness of the alginic acid gel layer can be measured by using an electron microscopic cross-sectional image, membrane thickness gage, ellipsomter, variable angle XPS or the like, and a value measured from an electron microscopic cross-sectional image is preferably used.

Alginic acid exists in nature as a cell wall-constituting polysaccharide or intercellular filling substance of brown algae, and can be obtained from the algae as raw materials. Examples of the brown algae as a raw material include brown algae belonging to Order Fucales, Family Durvilleaceas, Genus *Durvillea* (e.g., *D. potatorum*), Order Fucales, Family Fucaceae, Genus *Ascophyflum* (e.g., *A. nodosum*), Order Laminariales, Family Laminariaceae, Genus *Larminaria* (e.g., *Laminaria japonica, Laminaria longissima*), Order Laminariales, Family Laminariaceae, Genus *Eisenia* (e.g, *Eisenia bicyclis*), Order Laminariales, Family Laminariaceae, Genus *Ecklonia* (e.g., *Ecklonia cava, Ecklonia kurome*), and Order Laminariales, Family Lessoniaceae, Genus *Lessonia* (e.g., *L. flavikans*). Commercially available alginic acid can also be used. A G/M ratio of alginic acid is not particularly limited. A larger G/M ratio provides higher gel formation ability, and accordingly, a larger G/M ratio is more preferred. Specifically, the ratio may preferably be from 0.1 to 1, more preferably from 0.2 to 0.5.

The "cell adhesion gel layer" means hydrogel in the form of a layer having a cell adhesion property. The type of the gel is not particularly limited, and any gels may be used so long as cells can adhere thereto under an ordinary culture condition. Any hydrogel formed with a natural or non-natural gel-forming compound may be used. An extracellular matrix component gel in the form of a layer is preferably used.

The extracellular matrix is generally defined as "a stable biological structure existing extracellularly in an animal tissue, and is a complex aggregate formed by biological polymers which are synthesized by cells, and secreted and accumulated outside the cells" (Dictionary of Biochemistry (3rd edition), p. 570, Tokyo Kagaku Dojin), and the matrix plays roles of physically supporting cello, regulating cellular activities i.e., a role of transmitting extracellular information to a cell to change its activities) and the like. The 'extracellular matrix component' means a constituting ingredient of the extracellular matrix. Specific examples include collagen, elastin, proteoglycan, glucosaminoglycan (hyaluronic acid, chondroitin sulfate, dermatan sulfate, heparan sulfate, heparin, keratan sulfate and the like), fibronectin, laminin, vitronectin and the like. Among these, particularly preferred are collagen, atelocollagen, Matrigel (gel consisting of type IV collagen, laminin and heparan sulfate) and hyaluronic acid. The extracellular matrix component can be obtained in a conventional manner, and commercially available extracellular matrix components may also be used. The cell adhesion component can be gelled in a conventional manner. For example, when the cell adhesion component is collagen, a collagen gel can be obtained by incubating a 0.3 to 0.5% aqueous solution of collagen at 37° C. for from 10 to 20 minutes. A gelling agent may be used for the gelation of the extracellular matrix component, if needed.

The dry thickness of the cell adhesion gel layer is not particularly limited. For example, the thickness may preferably be from 0.005 to 0.3 µm, more preferably from 0.005 to 0.2 µm. The thickness of the cell adhesion gel layer is preferably measured under a sufficiently dried condition, and the thickness of the cell adhesion gel layer can be measured by using an electron microscopic cross-sectional image, membrane thickness gage, ellipsomter, variable angle XPS or the like, and a value measured from an electron microscopic cross-sectional image can be preferably used. When the cell adhesion gel layer is too thick, cracks may be generated during drying, and transfer of cells may become extremely difficult.

In order to laminate a cell adhesion component gel layer on a calcium alginate gel layer, the calcium alginate gel layer and the cell adhesion component gel layer may be separately prepared and then laminated. It is preferable to laminate an aqueous solution containing a cell adhesion component on an alginic acid gel layer and then the aqueous solution is allowed to form a gel, because it is difficult to detach the gel layer of the cell adhesion component from a vessel in which the gel layer of the cell adhesion component is formed (e,g., dish, petri dish and the like), since the gel layer of the cell adhesion component does not have sufficient strength for removal. An extremely thin cell adhesion gel layer can be conveniently obtained by immersing a calcium alginate layer in a solution of a cell adhesion component. For example, a calcium alginate gel prepared by the aforementioned method can be immersed in a commercially available 0.3 to 0.5% collagen aqueous solution, washed with water, and then dried to obtain such a layer.

Culture of cells using a carrier for cell culture comprising a calcium alginate gel layer can be performed specifically as follows. The carrier for cell culture is placed inside a petri dish or the like, then an appropriate culture medium (for example, D-MEM medium, MEM medium, HamF12 medium, HamF10 medium) is added to the petri dish to immerse the carrier for 5 minutes, and then the medium is exchanged. After this procedure is repeated three times, the culture system was left for 12 to 24 hours so that the culture medium can infiltrate into the carrier for cell culture. Then, the culture medium in the petri dish is discarded, cells are inoculated onto the cell adhesion gel layer of the carrier for cell culture, and further an appropriate culture medium (for example, D-MEM medium, MEM medium, HamF12 medium, HamF10 medium) is added to the petri dish. After the system is left at 37° C. for 1 to 2 hours so that the cells should adhere to the cell adhesion gel layer, the culture is continued at 37° C. During the culture, the culture medium may be exchanged, if needed. Usually, the culture medium is exchanged every 0.5 to 2 days of the culture. Cell culture obtained by culturing cells using the aforementioned carrier for cell culture contains the carrier for cell culture and a cell layer retained on the carrier for cell culture. According to a preferred embodiment, the cell layer retained on the carrier for cell culture is a cell layer formed on a cell adhesion gel layer laminated on a calcium alginate gel layer.

In order to detach cultured calls from cell culture, the calcium alginate gel layer may be solubilized. If necessary, the cell adhesion gel layer can also be simultaneously solubilized and removed. By performing such a treatment, cultured cells can be taken out as a sheet. In order to remove the carrier for cell culture according to the method of the present invention, a compound represented by the formula (I), or a polyphosphoric acid or a salt thereof can be preferably used at a concentration of from 10 nM to 100 mM, more preferably from 500 nM to 50 mM, particularly preferably from 1 mM to 10 mM. A compound represented by the formula (I) and a polyphosphoric acid or a salt thereof may be used in combination. For example, the solubilization treatment of the calcium alginate gel layer can be performed by immersing cell culture in an aqueous solution containing a compound represented by the formula (I), or a polyphosphoric acid or a salt thereof to remove cation components constituting the calcium alginate gel. Since a lot of phosphate ions usually exist in a medium for cell culture, the immersion is preferably performed by using an aqueous solution added with a compound represented by the formula (I) in an amount of 90 mol % or more based on the total mole number of polyvalent metal cations from a viewpoint of reduction of damage to cells. The concentration of the compound represented by the formula (I), or a polyphosphoric acid or a salt thereof is preferably from 90 mol % to 10000 mol %, more preferably from 90 mol % to 1000 mol %.

The aqueous solution containing a compound represented by the formula (I), or a polyphosphoric acid or a salt thereof used for detachment treatment may contain medium components, or a compound represented by the formula (I), or a polyphosphoric acid or a salt thereof may be added to the medium to perform the solubilization treatment of the calcium alginate gel layer. The time for the removal treatment utilizing a compound of the formula (I), or a polyphosphoric acid or a salt thereof is preferably 1 minute to 12 hours, most preferably 5 minutes to 2 hours, The aqueous solution containing a compound represented by the formula (I), or a polyphosphoric acid or a salt thereof for detachment may optionally contain a buffering agent, pH modifier, a medium composition or components thereof and the like. A temperature for the treatment is not particularly limited. The temperature is desirably within the usual temperature range for performing cell culture. When the method of the present invention is used for cell transfer operation for subculture, it is preferable to use trypsin together. The amount of trypsin used is preferably from 100 µg/l to 50 g/L, most preferably from 1 g/L to 10 g/L.

The solubilization treatment of the calcium alginate gel layer using a compound represented by the formula (I), or a polyphosphoric acid or a salt thereof is preferably performed by infiltrating the compound represented by the formula (I), or the polyphosphoric acid or a salt thereof from a porous membrane to bring the compound into contact with the gel layer. As a result of the above operation, the porous membrane and the calcium alginate gel layer can be easily separated, and cell culture can be easily detached from the porous membrane. It is unnecessary to completely remove the alginic acid gel layer by the solubilization treatment of the calcium alginate gel layer, and the calcium alginate gel may remain in the cultured cell obtained after the solubilization treatment. The calcium alginate gel layer may preferably be solubilized and thereby removed as much as possible. Further, it is also preferable to simultaneously remove the cell adhesion gel layer by the solubilization treatment.

The cell culture obtained by subjecting the calcium alginate gel layer to the solubilization treatment contains a cultured cell layer, and accordingly, the cell culture can be used for lamination or transfer of cell layers. The method for laminating a cell layer may be, for example, a method of culturing cells of which cell layer is adhered to preliminarily cultured cells with weighting and then solubilizing the calcium alginate gel, a method of laminating cell cultures obtained by solubilizing the calcium alginate gel layers, a method of laminating cultured cells obtained by solubilizing the calcium alginate gel layer on a cell layer separately prepared, and the like. The kinds of cells of the cell layers to be laminated may be the same or different. The number of the cell layers to be laminated is not particularly limited. Generally the number is from 1 to 10, preferably from 1 to 5, more preferably from 1 to 3. For transfer of a cell layer, the cell layer may be cultured under contact with weighting to another substrate for cell culture, and then the calcium alginate gel may be solubilized, or cell culture obtained by solubilizing the calcium alginate gel layer may be transferred on another medium. A preferred method for the lamination or transfer comprises the step of culturing cultured cells formed on a carrier for cell culture, of which layer is in contact with cells cultured beforehand or on another carrier for cell culture with weighting, and then dissolving the calcium alginate gel.

The weighting may be performed by any method in any degree so long as the cell layers can be sufficiently closely contacted in such a degree that unevenness should not be formed on the cell layer or carrier for cell culture surface on which cells are to be transferred. If cells are sealed by weighting, cells may be smothered. Therefore, at least either of the cell culture substrates to be transferred or that to receive the transfer preferably consists of a water-permeable gel, porous membrane, or a combination thereof. Further, for uniform transfer, weight should be applied so as to sufficiently cover the surface of the cell layer. However, uniform contact may disturb diffusion of oxygen, and therefore, weight may preferably be applied through non-fabric sheet (nylon, polyester, stainless steel and the like) or the like so as not to dusturb the diffusion of oxygen. The weight to be applied may be, for example, preferably from about 0.1 to 50 g/cm$^2$, more preferably from about 0.5 to 10 g/cm$^2$. The culture time of the cells under weighing is not particularly limited so long as sufficient transfer of cell can be achieved. The period of time is preferably from 4 to 72 hours, more preferably from 6 to 48 hours.

When the methods of the present invention are performed, the carrier for cell culture is preferably sterilized. The sterilization method is not particularly limited. For example, sterilization by radiation with, for example, electron beam, γ-ray, X-ray, and ultraviolet ray may be preferably used. An electron beam, γ-ray, and ultraviolet ray are more preferably used, and electron beam sterilization is particularly preferred. The exposure dose for the electron beam sterilization is preferably from 0.1 to 65 kGy, most preferably from 1 to 40 kGy. Chemical sterilization such as ethylene oxide gas sterilization and sterilization using a high temperature such as high pressure steamy gas sterilization are not preferred, because the cell adhesion layer and the alginic acid gel layer may be decomposed. The aforementioned sterilization methods may be used each alone or in combination. The same sterilization method may be applied repeatedly.

By using vascular endothelial cell layers or hepatocyte layers as the laminated cell layers, for example, a three-dimensional tissue structure of the liver can be constructed. The three-dimensional tissue structure can be used for, for example, in vitro permeability tests of drugs, and can also be utilized as a substitute model for an animal experiment or as an organ for transplantation. The laminated cell layers can be cultured under a culture condition suitable for the type of cells constituting the cell layer. For the culture, for example, D-MEM medium, MEM medium, HamF12 medium, HamrF10 medium and the like can be used as the medium.

EXAMPLES

The present invention will be more specifically explained by referring to the following examples. However the scope of the present invention is not limited to the following examples.

Example 1

Preparation of Carrier for Cell Culture (1) Preparation of Nylon Microfilter 13.7 g of 6-nylon was dissolved in 66.3 g of formic acid, left overnight, added with 20 ml of water and dispersed by using a homogenizer to obtain a nylon dope, The obtained nylon dope was applied on a stainless steel substrate with a thickness of 250 ml/m$^2$, and the coated substrate was immersed in a 45 weight % aqueous solution of formic acid. After the coated layer became sufficiently cloudy, the coated substrate was washed with running water to obtain a nylon microfilter. The nylon microfilter was stored in water without dryness.

(2) Formation of Calcium Alginate Layer

Moisture on the nylon microfilter obtained in the above (1) was Wiped with paper, the filter was immersed in a 0.1 M aqueous solution of calcium chloride, and a 1 weight % aqueous solution of sodium alginate was applied on the filter with a thickness of 100 ml/m$^2$. The coated substrate was immersed in an aqueous solution containing 0.1 M calcium chloride and 10 mg/l of WSC and washed with running water to obtain a nylon microfilter/calcium alginate laminate membrane. The thickness of the alginic acid gel layer dry membrane was 0.75 μm as measured from an electron microscopic cross-sectional image.

(3) Modification with Collagen Layer

Each of the simple calcium alginate membrane with glass substrate and the nylon microfilter/calcium alginate laminate membrane in a non-dried state obtained in the above (2) was immersed in a 10-fold aqueous dilution of Cellmatrix I-C produced by Nitta Gelatin) for 1 hour, washed with running water and dried to obtain a membrane modified with an extremely thin collagen layer. The total thickness of the collagen layer and the alginic acid gel layer was determined to be 0.8 µm from an electron micrograph, and the thickness of the collagen layer was calculated to be 0.05 µm as a difference of the total thickness and the alginic acid gel layer thickness of 0.75 µm.

(4) Sterilization

The membrane obtained in the above (3) was subjected to UV sterilization for 3 hours to obtain carrier for cell culture.

Example 2

Cell-culture Utilizing Carrier for Cell Culture

Cells were cultured by using the carrier for cell culture as follows.

(1) Materials

Used cell: CHL (Chinese Hamster Lung Cell)
Used medium: Eagle's minimum medium containing 10% bovine fetal serum Carrier for Cell Culture:

The carrier for cell culture prepared in Example 1, adhered to bottom surfaces of polystyrene cell culture dishes with double-sided tapes, and a polystyrene cell culture dishes alone as a comparative example were subjected to UV sterilization or electron beam sterilization. The operation, wherein the medium was added to the dishes to immerse the carrier for cell cultures for 5 minutes and then the medium was exchanged, was repeated three times, and then the dishes were left overnight to allow the medium to infiltrate into the carriers for cell culture. The combinations of the used carriers for cell culture and sterilization methods are shown in Table 1.

(2) Culture of Cells

The calls cultured beforehand were collected by trypsin treatment, and the cell density was adjusted to 50,000 cells/ml. After the medium in the cells and dishes was discarded, the cell suspension was inoculated into the dishes at a cell number of 10,000 cells/$cm^2$, and then the medium was added. Thereafter, the cells were cultured at 37° C. for two days by using a $CO_2$ incubator.

(3) Detachment of Cell Layer

The samples obtained by the culture were immersed in each of the following seven kinds of detachment solutions and non-detachment solutions, and then the cell layers were pulled with a pair of tweezers to examine state of detachment of the cell layers from the carriers for cell culture. A period of time required for the detachment of each cell layer was measured. Then, the cell sheets detached with an immersion time in a detachment solution of 30 minutes was placed on a polystyrene cell culture dish, added with the medium and cultured at 37° C. for one day by using a $CO_2$ incubator. The cells were stained with trypan blue and observed under an optical microscope. The results are shown in Table 1. The use of detachment agents of the present invention provided favorable detachment characteristics, that is, high survival rate of the cells and non-stimulative property (i.e., no cell deformation due to stimulation) was successfully confirmed.

Detachment Solutions
(i) Distilled water
(ii) Eagle's minimum medium (MEM)
(iii) MEM added with 1.5 M EDTA
(iv) MEM added with 3 g/l of sodium hexametaphosphate (HMPA)
(v) MEM added with 3 mM 1-hydroxyethane-1,1-diphosphoric acid (HEDP)

As for the detachment solutions (iii) to (v), pH was adjusted to that of the detachment solution (ii) with NaOH or HCl after the chemicals were added.

TABLE 1

| Detachment solution | Detachment time | State of cells after detachment | | |
|---|---|---|---|---|
| | | Survival rate | Morphology of survived cells | |
| (i) $H_2O$ | 20 minutes | 5% or less | Deformed roundly | Comparative |
| (ii) MEM | Not detached | — | — | Comparative |
| (iii) MEM + EDTA | 15 minutes | 50 to 70% | Half was deformed roundly | Comparative |
| (iv) MEM + HMPA | 10 minutes | 90% or more | Not deformed | Invention |
| (v) MEM + HEDP | 20 minutes | 90% or more | Not deformed | Invention |

Example 3

Transfer of Cell Layer

The samples obtained by the culture on the carriers for cell culture in Example 2 were taken out together with the carriers for cell culture, and placed on polystyrene cell culture dishes in such a manner that the cell layer surfaces contacted with the dishes, and foamed urethane filters having a thickness of 3 mm and stainless steel plates were placed thereon in this order. The weight of each stainless steel plate was adjusted so that the total weight including the weight of the urethane filter became 0.8 g/$cm^2$. Then, the samples were immersed in the detachment solution (iii), (iv) or (v) mentioned in Example 2 for 10 minutes, and after the solution was replaced with the medium, culture was performed at 37° C. for one day by using a $CO_2$ incubator. The cultures were immersed in the same detachment solutions for 20 minutes, and then the carriers for cell culture were detached by pulling with a pair of tweezers. Then, the solutions were replaced with the medium, and culture was continued at 37° C. for one day by using a $CO_2$ incubator. The cells were stained with trypan blue and then observed under an optical microscope. The results are shown in Table 2. Favorable results were obtained with the detachment solutions of the present invention. In the sample where the weight was applied only by using the stainless steel plates without using the nylon non-woven fabric and the sample where the detachment solution (i) was used, the cells died during the transfer operation. Further, in the sample where the detachment solution (ii) was used, transfer was not successful.

TABLE 2

| Detachment solution | State of cells after detachment | | |
|---|---|---|---|
| | Survival rate | Morphology of survived cells | |
| (iii) MEM + EDTA | 50 to 70% | Half was deformed roundly | Comparative |
| (iv) MEM + HMPA | 90% or more | Not deformed | Invention |
| (v) MEM + HEDP | 90% or more | Not deformed | Invention |

Example 4

Lamination of Cell Layers

Figure 1:
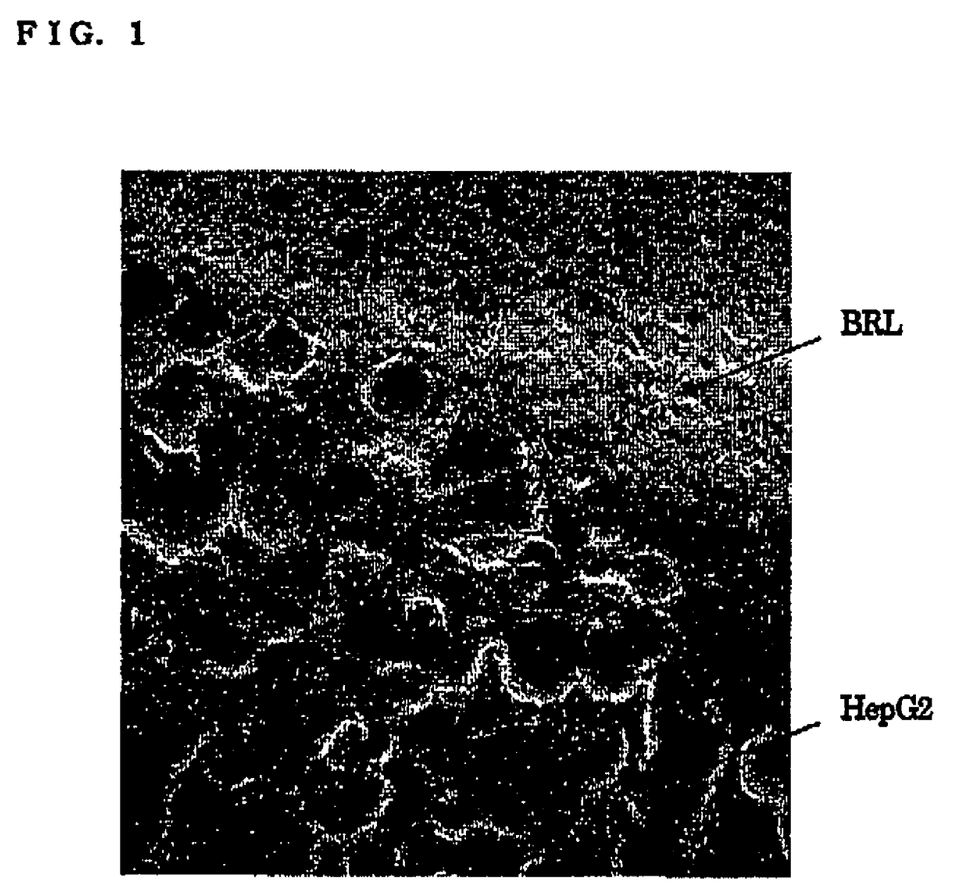
FIG. 1 is an optical microscopic photograph showing the result of expression of cytochrome P-450 3A in laminated cells obtained by laminating cells which were detached by using a detachment solution of the present invention.

In the same manner as that of Example 2, HepG2 (human liver cancer derived cells) was cultured on the carrier for cell culture of Example 1, and BRL (Buffalo Rat Liver 3A, ATCC No. CRL 1442) was cultured on a polystyrene cell culture dish. Cell layers were transferred on the cells cultured on the dishes by using the detachment solution (v) mentioned in Example 2 in the same manner as that of Example 3 to obtain laminated cells. These laminated cells were cultured in the medium for 90 hours, added with 7-benzoyl-4-(trifluoromethyl)coumarin (BFC), and cultured for two days, and then 7-hydroxy-4-(trifluoromethyl)coumarin (HFC) produced through metabolism by cytochrome P-450 3A was observed with a fluorescence microscope. Fluorescence derived from HFC was observed in the portions of HepG2 (FIG. 1).

Example 5

Influence of Chelating Agent on Cultured Cells

CHL cells cultured beforehand were collected by trypsinization, and the cell density was adjusted to 50000 cells/ml. This cell suspension was inoculated on a polystyrene cell culture dish at a cell number of 10000 cells/cm², and each of the following media was added. Then, the cells were cultured at 37° C. for two days by using a CO₂ incubator. The results of evaluation of stimulative property on the cells based on morphology and proliferation property of the cultured cells are shown in Table 3. The results are represented by using the result obtained for the cells cultured with the medium a mention d in the table as a standard. As for the proliferation property, the cell number exceeding 100% is indicated with ⊚, the cell number of 90 to 100% is indicated with ○, slight degradation to 70 to 90% is indicated with Δ, and degradation to 70% or less is indicated with X. Further, as for the cell morphology, 70% or more of not rounded cells are indicated with ○, 30 to 70% of not rounded cells are indicated with Δ, and 30% or less of not rounded cells are indicated with X.
Medium a: Eagle's minimum medium (MEM)
Medium b: MEM added with 1.5 mM EDTA
Medium c: MEM added with 1.5 mM GEDTA
Medium d: MEM added with 1.5 mM diethylenetriamine-N,N,N',N,N-pentaacetic acid (DTPA)
Medium e: MEM added with 3 g/l of sodium hexametaphosphate (HMPA)
Medium f: MEM added with 3 mM 1-hydroxyethane-1,1-diphosphoric acid (HEDP)
Medium g: MEM added with 1.5 mM ethylenediamine-N,N,N',N'-tetrakis(methylenephosphoric acid) (EDTPO)

As for the media b to f, pH was adjusted to that of the medium a with NaOH or HCl after the chemicals were added.

TABLE 3

| | Medium | State of cells | | |
|---|---|---|---|---|
| | | Proliferation rate | Morphology | |
| a | MEM | ○ (type) | ○ | Comparative |
| b | MEM + EDTA | X | X | Comparative |
| c | MEM + GEDTA | Δ | Δ | Comparative |
| d | MEM + DTPA | X | X | Comparative |
| e | MEM + HMPA | ○ | ○ | Present Invention |
| f | MEM + HEDP | ⊙ | ○ | Present Invention |
| g | MEM + EDTPO | ○ | ○ | Present Invention |

Example 5

Subculture by Detachment with Trypsin

Five tissue culture flasks (3013 produced by FALCON) were prepared, in which CHL cells were cultured beforehand and proliferated to such a degree that the cells occupied about 80% of the bottom surfaces of the flasks. The medium in the flasks was removed by sucking using an aspirator, and the cell surfaces were washed with a small amount of trypsin solution (16050-065 produced by GIBCO). After the washing, 2 ml of the trypsin solution was added again to the flasks, and the flasks were moved to a CO₂ incubator (CO₃, 37° C.). After 0.5, 1, 2, 3 and 4 minutes, one culture flask for each time was taken out, and the single cell isolation was performed by using a pipette. After the calls were collected by centrifugation, the cells were inoculated into flasks containing fresh medium in a number of 200,000 cells per flask. The cells were cultured at 37° C. under 5% CO₂ for 4 days, and the state of the cells was observed by using a phase contrast inverted microscope. As a result, cell aggregations were formed after 0.5 minute of trypsinization, and cell growth was clearly delayed after 2 to 4 minutes of trypsinization. Normal cell growth was observed only after trypsinization of 1 minute. It was thus concluded that subculture by detachment with trypsin required an optimum treatment time, and the most favorable subculture was not expected with a treatment time longer or shorter than the optimum time.

What is claimed is:
1. A method for detaching a carrier for cell culture from cultured cells formed on a surface of said carrier for cell culture, which comprises the step of bringing the carrier for cell culture into contact with a compound represented by the following formula (I) or a polyphosphoric acid or a salt thereof:

$$MO_3P-L^{11}-PO_3M$$

wherein $L^{11}$ represents at least one substituted or unsubstituted divalent hydrocarbon group; and M represents hydrogen atom or a cation, wherein the carrier for cell culture comprises a calcium alginate gel layer, to thereby detach the carrier for cell culture from the cultured cells.
2. A method for culturing a layer of cells by using a carrier for cell culture which comprises the steps of:
(1) culturing cells on a carrier for cell culture comprising a calcium alginate gel layer; and (2) bringing the cultured cells and carrier for cell culture into contact with a compound represented by the following formula (I) or a polyphosphoric acid or a salt thereof, $MO_3P\text{-}L^{11}\text{-}PO_3M$ wherein $L^{11}$ represents at least one substituted or unsubstituted divalent hydrocarbon group; and M represents hydrogen atom or a cation, to thereby detach the carrier from the cultured layer of cells.

3. A method for transferring a cell culture, which comprises the steps of:
  (1) culturing cells on a first carrier for cell culture comprising a calcium alginate gel layer,
  (2) bringing the cell culture into contact with a surface of a second carrier for cell culture with weighting such that the cells adhere to both surfaces; and
  (3) bringing the cell culture obtained in the aforementioned step (2) into contact with a compound represented by the following formula (I) or a polyphosphoric acid or a salt thereof;

$MO_3P\text{-}L^{11}\text{-}PO_3M$

Wherein $L^{11}$ represents at least one substituted or unsubstituted divalent hydrocarbon group; and M represents hydrogen atom or a cation, to detach the first carrier for cell culture.

4. A method for laminating cultured cell layers, which comprises the steps of:
  (1) culturing cells on a carrier for cell culture comprising a calcium alginate gel layer to provide a first cultured cell layer;
  (2) bringing the first cultured cell layer into contact with a second cultured cell layer with weighting such that the first cell layer and the second cell layer adhere to each other; and
  (3) bringing the adhered cell layers and carrier for cell culture obtained in the aforementioned step (2) into contact with a compound represented by the following formula (I) or a polyphosphoric acid or a salt thereof:

$MO_3P\text{-}L^{11}\text{-}PO_3M$ wherein $L^{11}$ represents at least one substituted or unsubstituted divalent hydrocarbon group; and M represents hydrogen atom or a cation, to thereby detach the carrier for cell culture and obtain laminated cultured cell layers.

5. The method according to claim 1, wherein the carrier for cell culture comprises laminated calcium alginate gel layer and cell adhesion gel layer.

6. The method according to claim 1, wherein the divalent hydrocarbon group is a substituted or unsubstituted methylene group.

7. The method according to claim 1, wherein the compound represented by the formula (I) is a compound represented by the following formula (II):

$$MO_3P\text{—}L^{21}\text{—}\underset{\underset{R^{21}}{|}}{N}\text{—}L^{23}\text{—}\underset{\underset{R^{22}}{|}}{N}\text{—}L^{22}\text{—}PO_3M$$

wherein $L^{21}$, $L^{22}$ and $L^{23}$ independently represent a divalent hydrocarbon group; $R^{21}$ and $R^{22}$ independently represent a substituted or unsubstituted alkyl group, or a substituted or unsubstituted aryl group; and M represents hydrogen atom or a cation.

8. The method according to claim 1, wherein the compound represented by the formula (I) is a compound represented by the following formula (III):

$$\begin{array}{c}MO_3P\text{—}L^{32} \qquad L^{34}\text{—}PO_3M \\ | \qquad\qquad | \\ MO_3P\text{—}L^{31}\text{—}N\text{—}L^{35}\text{—}N\text{—}L^{33}\text{—}PO_3M\end{array}$$

wherein $L^{31}$, $L^{32}$, $L^{33}$, $L^{34}$, and $L^{35}$ represent a divalent hydrocarbon group; and M represents hydrogen atom or a cation.

9. The method according to claim 1, wherein the carrier for cell culture is brought into contact with the compound represented by formula (I) for a period of from 5 minutes to 2 hours to effect a removal treatment.

10. The method according to claim 1, wherein the compound of formula (I) is 1-hydroxyethane-1,1-diphosphoric acid.

* * * * *